US012697456B2

(12) United States Patent
Frerichs et al.

(10) Patent No.: US 12,697,456 B2
(45) Date of Patent: *Aug. 4, 2026

(54) BREATHING MASK INTERFACE WITH SMALL REQUIRED OPERATING FORCE

(71) Applicant: Loewenstein Medical Technology S.A., Luxembourg (LU)

(72) Inventors: Arnold Frerichs, Buxtehude (DE); Martin Bechtel, Winsen/Luhe (DE); Martin Eifler, Glueckstadt (DE); Joachim Gardein, Icod de los Vinos (ES)

(73) Assignee: Loewenstein Medical Technology S.A., Luxembourg (LU)

( * ) Notice: Subject to any disclaimer, the term of this patent is extended or adjusted under 35 U.S.C. 154(b) by 91 days.

This patent is subject to a terminal disclaimer.

(21) Appl. No.: 18/653,372

(22) Filed: May 2, 2024

(65) Prior Publication Data

US 2024/0277964 A1     Aug. 22, 2024

Related U.S. Application Data

(63) Continuation of application No. 16/008,254, filed on Jun. 14, 2018, now Pat. No. 12,005,191.

(30) Foreign Application Priority Data

Jun. 19, 2017     (DE) .......................... 102017005691.9
Jun. 19, 2017     (DE) .......................... 102017005692.7
(Continued)

(51) Int. Cl.
*A61M 16/06*     (2006.01)
*A61M 16/08*     (2006.01)

(52) U.S. Cl.
CPC ........ *A61M 16/0816* (2013.01); *A61M 16/06* (2013.01); *A61M 16/0605* (2014.02);
(Continued)

(58) Field of Classification Search
CPC .......................................... A61M 16/06–0683
See application file for complete search history.

(56) References Cited

U.S. PATENT DOCUMENTS

| 3,441,020 A | 4/1969 | Aasen |
| 5,853,002 A | 12/1998 | Kawasaki |
| (Continued) | | |

FOREIGN PATENT DOCUMENTS

| DE | 102005041716 A1 | 4/2006 |
| DE | 102005041717 A1 | 4/2006 |
| EP | 1632262 B1 | 6/2016 |

*Primary Examiner* — LaToya M Louis
(74) *Attorney, Agent, or Firm* — Abel Schillinger, LLP

(57)     ABSTRACT

A respiratory mask with an interface for the connection of at least two components, wherein the interface is round or oval and has a maximum diameter, and the components each make available at least one subregion of the interface. The component has a grip part which extends radially outward from the subregion and which is configured as a pressing surface or gripping means for fingers or the hand of an operator, wherein the component has two grip parts, wherein the subregions are in form-fit engagement with each other in an assembled state and are movable about a rotation axis (DA), for which purpose the grip part is rotatable to different rotation positions relative to the two grip parts.

20 Claims, 10 Drawing Sheets

(30)          Foreign Application Priority Data

| | | | |
|---|---|---|---|
| Jun. 19, 2017 | (DE) | ......................... | 102017005693.5 |
| Jun. 19, 2017 | (DE) | ......................... | 102017005694.3 |
| Jun. 19, 2017 | (DE) | ......................... | 102017005703.6 |
| Jun. 19, 2017 | (DE) | ......................... | 102017005704.4 |

(52) U.S. Cl.
CPC .... *A61M 16/0611* (2014.02); *A61M 16/0633*
(2014.02); *A61M 16/0638* (2014.02); *A61M 16/0825* (2014.02); *A61M 16/0683* (2013.01); *A61M 2205/582* (2013.01); *A61M 2205/583* (2013.01); *A61M 2209/082* (2013.01); *A61M 2209/088* (2013.01)

(56)               References Cited

U.S. PATENT DOCUMENTS

| | | | |
|---|---|---|---|
| 7,931,025 | B2 | 4/2011 | Eaton |
| 8,042,542 | B2 | 10/2011 | Ging |
| 8,051,855 | B2 | 11/2011 | Ho |
| 8,783,253 | B2 | 7/2014 | Flaherty |
| 9,616,190 | B2 | 4/2017 | Rummery |
| 9,950,131 | B2 | 4/2018 | Ng |
| 9,981,102 | B2 | 5/2018 | Veliss |
| 9,987,451 | B2 | 6/2018 | Stegman |
| 10,034,994 | B2 | 7/2018 | Mcauley |
| 10,118,009 | B2 | 11/2018 | Grashow |
| 10,500,363 | B2 | 12/2019 | Raje |
| 2008/0210241 | A1 | 9/2008 | Schulz |
| 2008/0230066 | A1 | 9/2008 | Chandaria |
| 2008/0230068 | A1 | 9/2008 | Rudolph |
| 2009/0126739 | A1 | 5/2009 | Ng |
| 2011/0265796 | A1 | 11/2011 | Amarasinghe |
| 2012/0204869 | A1 | 8/2012 | Gunaratnam |
| 2012/0204870 | A1 | 8/2012 | Mcauley |
| 2013/0228173 | A1 | 9/2013 | Bush |
| 2013/0284178 | A1 | 10/2013 | Eaton |
| 2014/0083431 | A1 | 3/2014 | Burz |
| 2014/0166018 | A1 | 6/2014 | Dravitzki |
| 2014/0202463 | A1 | 7/2014 | Ging |
| 2014/0305433 | A1 | 10/2014 | Rothermel |
| 2015/0352308 | A1 | 12/2015 | Cullen |
| 2016/0279371 | A1 | 9/2016 | Dravitzki |
| 2016/0367778 | A1 | 12/2016 | Eves |
| 2017/0080173 | A1 | 3/2017 | Barlow |
| 2017/0128687 | A1 | 5/2017 | Price |
| 2017/0274168 | A1 | 9/2017 | Kwok |
| 2017/0333657 | A1 | 11/2017 | Stephenson |
| 2018/0001046 | A1 | 1/2018 | Rummery |
| 2018/0021536 | A1 | 1/2018 | Ng |
| 2018/0043127 | A1 | 2/2018 | Matula |
| 2018/0250485 | A1 | 9/2018 | Zhan |

BREATHING MASK INTERFACE WITH SMALL REQUIRED OPERATING FORCE

CROSS-REFERENCE TO RELATED APPLICATIONS

The present application is a continuation of patent application Ser. No. 16/008,254, filed Jun. 14, 2018, which claims priority under 35 U.S.C. § 119 of German Patent Application Nos. 102017005691.9, 102017005692.7, 102017005693.5, 102017005694.3, 102017005703.6, 102017005704.4, and 102017005705.2, all filed on Jun. 19, 2017. The entire disclosures of these applications are expressly incorporated by reference herein.

BACKGROUND OF THE INVENTION

In a respiratory mask, for example a breathing mask or any other kind of breathing interface, a releasable and rotatable adapter for a hose attachment is usually arranged in the main body of the mask. Since the adapter has to be easy to exchange/clean, it is releasable, for example via a rotary locking connection. The invention starts out from an operating element of a respiratory mask with an interface. The operating element has a grip part which is rotatable about a rotation axis and which has a circumferential gripping surface. The grip part can be brought to different rotation positions, as a result of which the interface is operated. Locking elements are additionally present in the region of the interface. The respiratory masks of DE 10 2005 041 716 A1 and of DE 10 2005 041 717 A1 have examples of such an interface.

Depending on the configuration of the operating elements, it is sometimes necessary to be able to transmit high operating forces. This is particularly the case with purely mechanical operating elements if an additional locking means is provided. If operating elements that are actuated by rotation are provided only with a circumferential gripping surface, then the operating elements have to be of quite considerable diameter in order to be able to transmit the high operating forces safely and in an ergonomically acceptable manner.

The respiratory masks of DE 10 2005 041 716 A1 and of DE 10 2005 041 717 A1 are constructed from a large number of components. This results in a very solid and heavy design.

SUMMARY OF THE INVENTION

The object of the present invention is to make available an operating element of the type in question which allows high operating forces to be transmitted by what is nonetheless a delicate construction.

This object is achieved by the features of the independent claim. Advantageous embodiments and developments of the invention can be gathered from the dependent claims or from the description.

According to the invention, it is proposed that, instead of the circumferential gripping surface of DE 10 2005 041 716 A1 and of DE 10 2005 041 717 A1, a radially outwardly extending grip part is integrally formed on the securing ring, which grip part is configured and suitable for serving as a pressing surface or gripping means for fingers or the hand of an operator.

The invention therefore relates to a respiratory mask with an interface for the connection of at least two components, wherein the interface is round or oval and has a maximum diameter (D), and the components each make available at least one subregion of the interface, characterized in that the component has a grip part which extends radially outward from the subregion and which is configured as a pressing surface or gripping means for fingers or the hand of an operator (B), wherein the component has two grip parts which extend radially outward from the subregion and which are configured as a pressing surface or gripping means for fingers or the hand of an operator, wherein the subregions are in form-fit engagement with each other in an assembled state and are movable about a rotation axis, for which purpose the grip part is rotatable to different rotation positions relative to the two grip parts.

The grip parts are therefore intended to be dimensioned such that the fingers of an operator find sufficient space on them.

In this way, it is easily possible for the operator to be able to transmit radial forces and also axial forces to the interface. Overall, the transmission of high operating forces is thus possible, wherein the diameter of the circumferential gripping surface does not have to be enlarged. This is greatly conducive to an attractive and slim design of the whole respiratory mask.

The invention is also characterized in that the fingers of an operator find sufficient space thereon.

The invention is also characterized in that a grip part is configured as part of the forehead support and is formed integrally with the forehead support, wherein the forehead support additionally has contact locations for the harness.

The invention is also characterized in that two grip parts are configured as part of the body and are formed integrally with the body, wherein the grip parts additionally have contact locations for the harness.

The invention is additionally characterized in that the surface of the grip parts is provided with friction-enhancing means (for example knobs or ribs) in order to improve the haptics.

The invention is preferably characterized in that the interface serves for the connection of three components, wherein the components are mask body, hose connector and forehead support.

The invention is also characterized in that the grip part is longer than the diameter (D) of the interface.

The grip part is the carrier of the forehead support.

The diameter (D) of the interface is the maximum diameter (D) of the cutout in the component (3).

The invention is alternatively also characterized in that two grip parts are each 50%-200% long the dimension of the diameter (D) of the interface.

The invention is additionally also characterized in that two grip parts are arranged symmetrically opposite each other on the component.

The two grip parts (7, 9) can also be arranged at an angle to the component (3).

The invention is also characterized in that insertion bevels are provided in the region of the interface.

The invention is preferably also characterized in that, in the region of the interface, locking means are provided in the subregions.

The invention is additionally also characterized in that, in the region of the interface, at least two locking means, which are arranged symmetrically, are provided in the subregions.

The invention is alternatively also characterized in that the insertion bevels and the locking means are configured and arranged such that the operating forces needed to release the lock are higher than the operating forces needed to close the lock.

The invention is also characterized in that the components have at least one pointer (Z) and at least one symbol (S), wherein at least one pointer (Z) can be aligned with at least one symbol (S) by rotation of the grip part, wherein the symbol (S) is positionally fixed and the pointer (Z) is configured to be rotatable relative to the symbol (s).

The invention is not restricted to the exemplary embodiment or embodiments given above. They have only been used for explaining the basic idea of the invention in general. Rather, the invention can also accept within the scope of its protection exemplary embodiments or forms other than those described above. In that case, the invention may also have in particular features that represent a combination of individual features of the respective claims.

BRIEF DESCRIPTION OF THE DRAWINGS

The invention is explained below on the basis of exemplary embodiments and with reference to the figures, in which:

FIG. 6 shows a top view of the forehead support shown in FIG. 4,

DETAILED DESCRIPTION OF EXEMPLARY EMBODIMENTS

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description in combination with the drawings making apparent to those of skill in the art how the several forms of the present invention may be embodied in practice.

Figure 1:
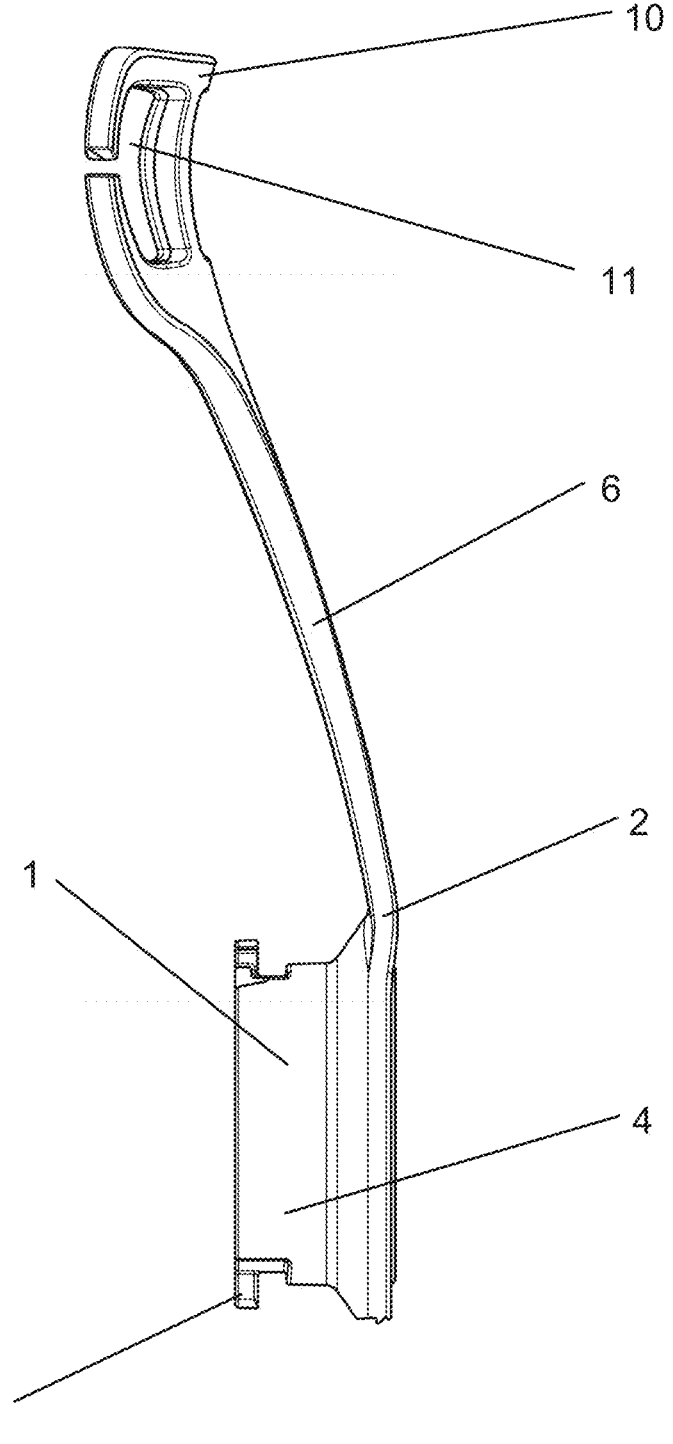
FIG. 1 shows a side view of a respiratory mask.
Figure 2:
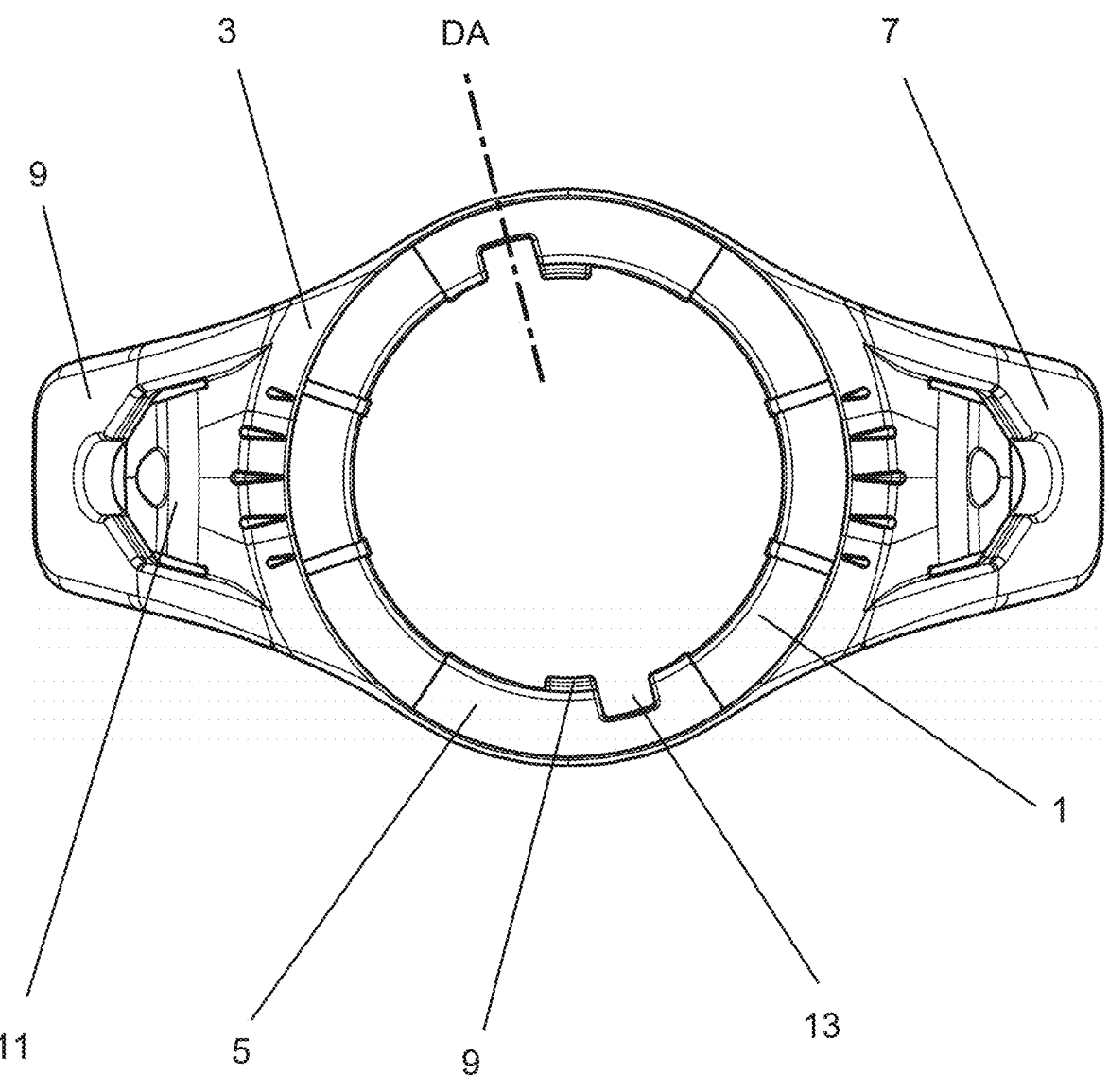
FIG. 2 shows a front view of the respiratory mask shown in FIG. 1.

FIG. 1 and FIG. 2 show the respiratory mask with an interface (1) for the connection of at least two components (2, 3). The interface (1) is round or oval, for example, and has a maximum diameter (D). The components (2, 3) each make available at least one subregion (4, 5) of the interface. The component (2) has a grip part (6) which extends radially outward from the subregion (4) and which is configured as a pressing surface or gripping means for fingers or the hand of an operator (B). The component (3) has two grip parts (7, 9) which extend radially outward from the subregion (5) and which are configured as a pressing surface or gripping means for fingers or the hand of an operator (B). The subregions (4, 5) are in form-fit engagement with each other in an assembled state and are movable about a rotation axis (DA). For this purpose, the grip part (6) is rotatable to different rotation positions relative to the two grip parts (7, 9). The figures reveal the rotational symmetry through 180° about an axis (DA) located at the center point of the inner radius and protruding perpendicularly from the drawing plane. The symmetry means that the parts can be assembled in any desired orientation. By coding of the bayonet position, e.g. in the case of three bayonets, an asymmetrical configuration is also possible.

The grip parts (6 7, 9) are dimensioned such that the fingers of an operator find sufficient space on them.

The grip part (6) is configured as part of the forehead support (10) and is formed integrally with the forehead support (10), wherein the forehead support additionally has contact locations (11) for a harness (not shown).

The two grip parts (7, 9) are configured as part of the body and are formed integrally with the body (3). The grip parts additionally have contact locations (11) for a harness.

The interface (1) serves for the connection of three components (2, 3), wherein the components are mask body (3), hose connector (not shown) and forehead support (2). The hose connector has, for example, a ball-joint-shaped region which is at least partially surrounded by and held by the forehead support (2). The ball-joint-shaped region is preferably received by the subregion (4).

The grip part (6) is longer than the diameter (D) of the interface.

The two grip parts (7, 9) are of similar length (50%-200%) as the dimension of the diameter (D) of the interface.

The two grip parts (7, 9) are here arranged symmetrically opposite each other on the component (3).

In the region (4, 5) of the interface, insertion bevels (13) and locking means (12) are provided, which are here arranged symmetrically in the region (4, 5). The components (2, 3) can therefore be assembled in any desired orientation relative to each other.

The insertion bevels and the locking means (12, 13) are configured and arranged such that the operating forces needed to release the lock are higher than the operating forces needed to close the lock. This permits securing of the connection of the components (2, 3).

The bayonet on the forehead support is configured pointing radially outward, and corresponding recesses are provided at the inner radius in the mask body. The bayonet on the securing ring locks in the mask body in the direction of joining, which facilitates finding and guiding.

Figure 3:
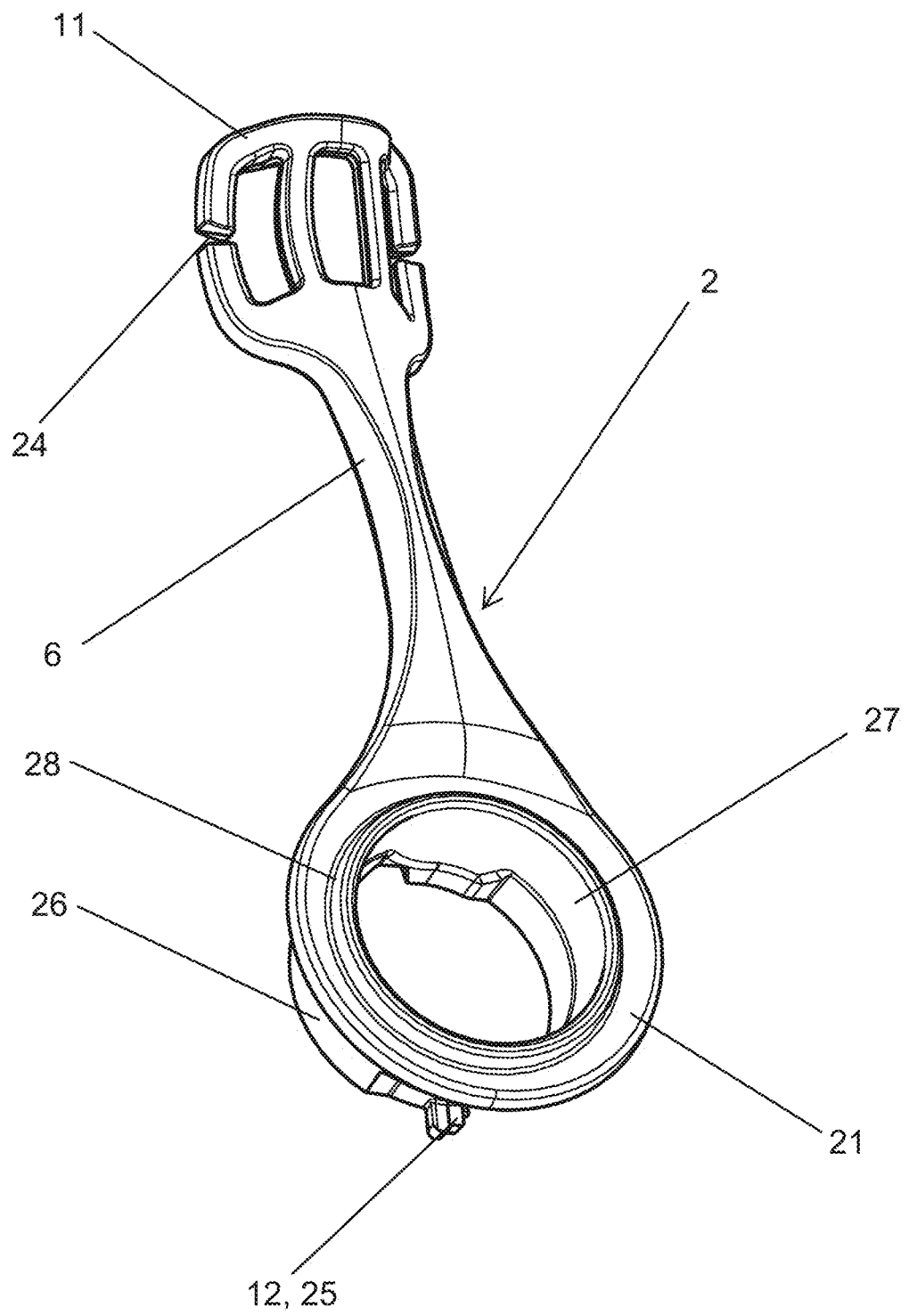
FIG. 3 shows the forehead support of the respiratory mask shown in FIG. 1.

FIG. 3 shows an embodiment of a forehead support (2) according to the invention. The base of the forehead support (2) is formed by the forehead support connector (21), with which the forehead support (2) is secured to the mask body (3). A web (6) connects the forehead support connector (21) to the strap coupling (11) at the head of the forehead support (2). The strap coupling (11) is composed of two, preferably three, alternatively four cutouts in the structure of the forehead support (2), said cutouts being arranged horizontally alongside one another and extending longitudinally in a vertical direction. The two outer cutouts each have an additional gap (24) in the outwardly directed structure of the forehead support (2). These gaps (24) can be used for engaging the holding straps, at the forehead height of a patient, into the strap coupling (11). Alternatively, the strap can also be guided through the centrally positioned cutout.

Other embodiments of the strap coupling (11) are also conceivable. For example, it can also be realized by only two cutouts with an additional gap (24).

In the embodiment shown, the web (6) is significantly reduced in width compared to the head part with strap coupling (11) and to the forehead support connector (21). This permits an attractive, slim design and saves on material.

To complete the bayonet catch provided in the mask body (3), the forehead support connector (21) offers a number of closure teeth (12, 25) corresponding in position and number to the channels (8, 13) present in the mask body. These closure teeth (12, 25) protrude radially outward from the outer contour of the connection ring (4, 26) and in turn each have a further radially outwardly directed tooth which, together with the locking tooth (14) in the mask body (3), ensures that mask body (3) and forehead support (2) are locked in the intended position. The inner contour of the forehead support connector (21) is configured as a ball cage (27), which can movably bear the attachment piece (33). Toward the attachment piece (33), the ball cage (27) is delimited by an outwardly narrowing ring structure (28).

Figure 4:
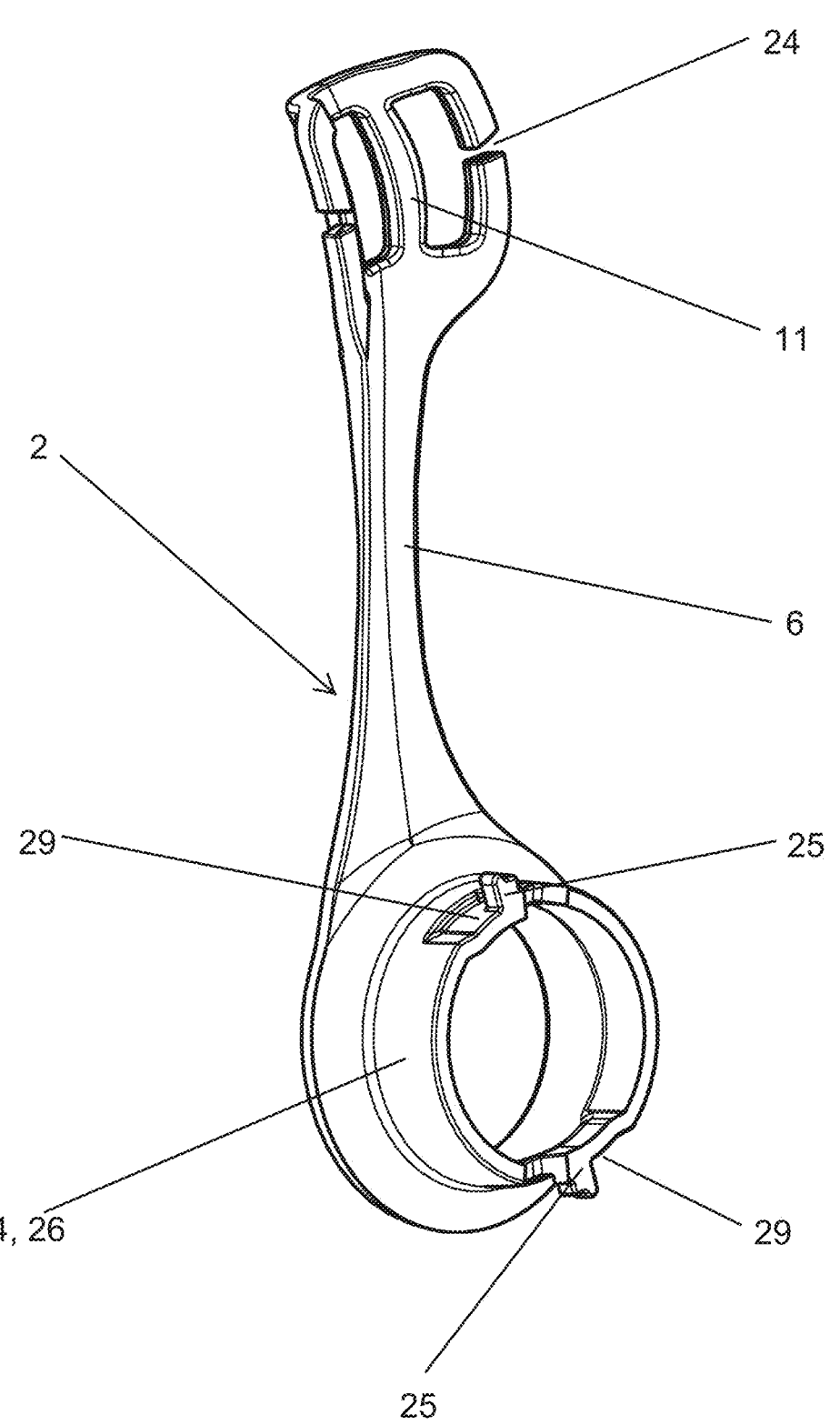
FIG. 4 shows a perspective rear view of the forehead support from FIG. 3.

FIG. 4 shows a perspective view of a forehead support (2) from the rear. The illustrated forehead support (2) has two closure teeth (25). However, a larger number of closure teeth (25) matching the respective mask body (3) is also conceivable. Cutouts (29) can be seen in the outer contour of the connection ring (26) alongside the closure teeth (25). These cutouts (29) serve as additional outflow channels and lead the exhaled gases around the respective closure tooth (25) to the corresponding channel (8) arranged in the mask body (3). It is additionally conceivable for such a cutout (29) also to be used as a mechanical coding for a defined orientation of mask body (3), forehead support (2) and mask cushion (3). For this, the structure of the mask body (3) must be suitably permeable in the region of its mechanical coding (15).

Figure 5:
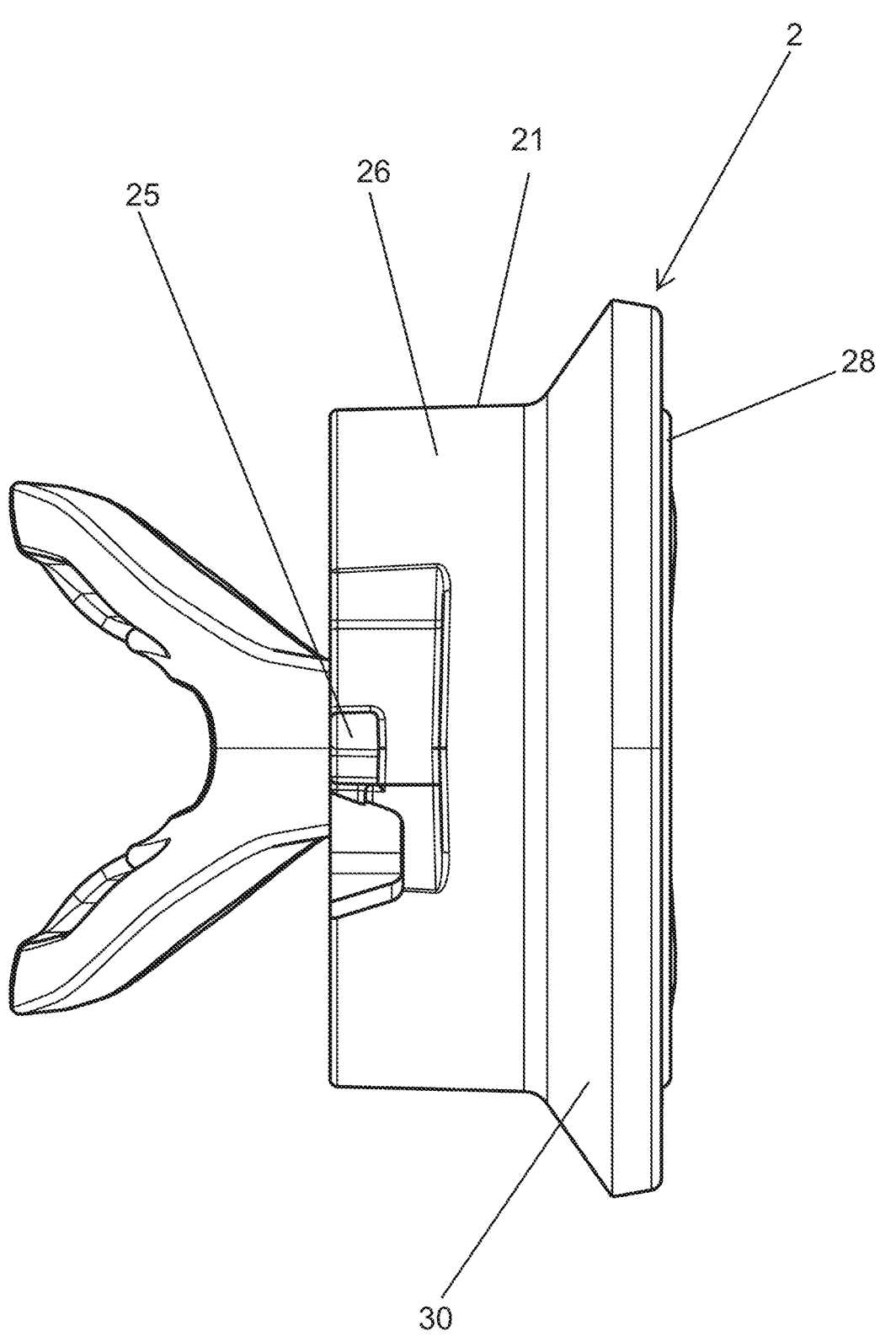
FIG. 5 shows a bottom view of the forehead support shown in FIG. 4.

The forehead support (2) from FIG. 4 is shown from below in FIG. 5. The latter reveals the outer contour of the forehead support connector (21), which is adapted to the inner contour of the mask body (3) and which is likewise composed of a ring and a funnel. This contour forms the discharge surface (30) on the forehead support side and, together with the inner surface of the mask body (3), defines the shape of the discharge channels and the exhalation gaps.

Figure 6:
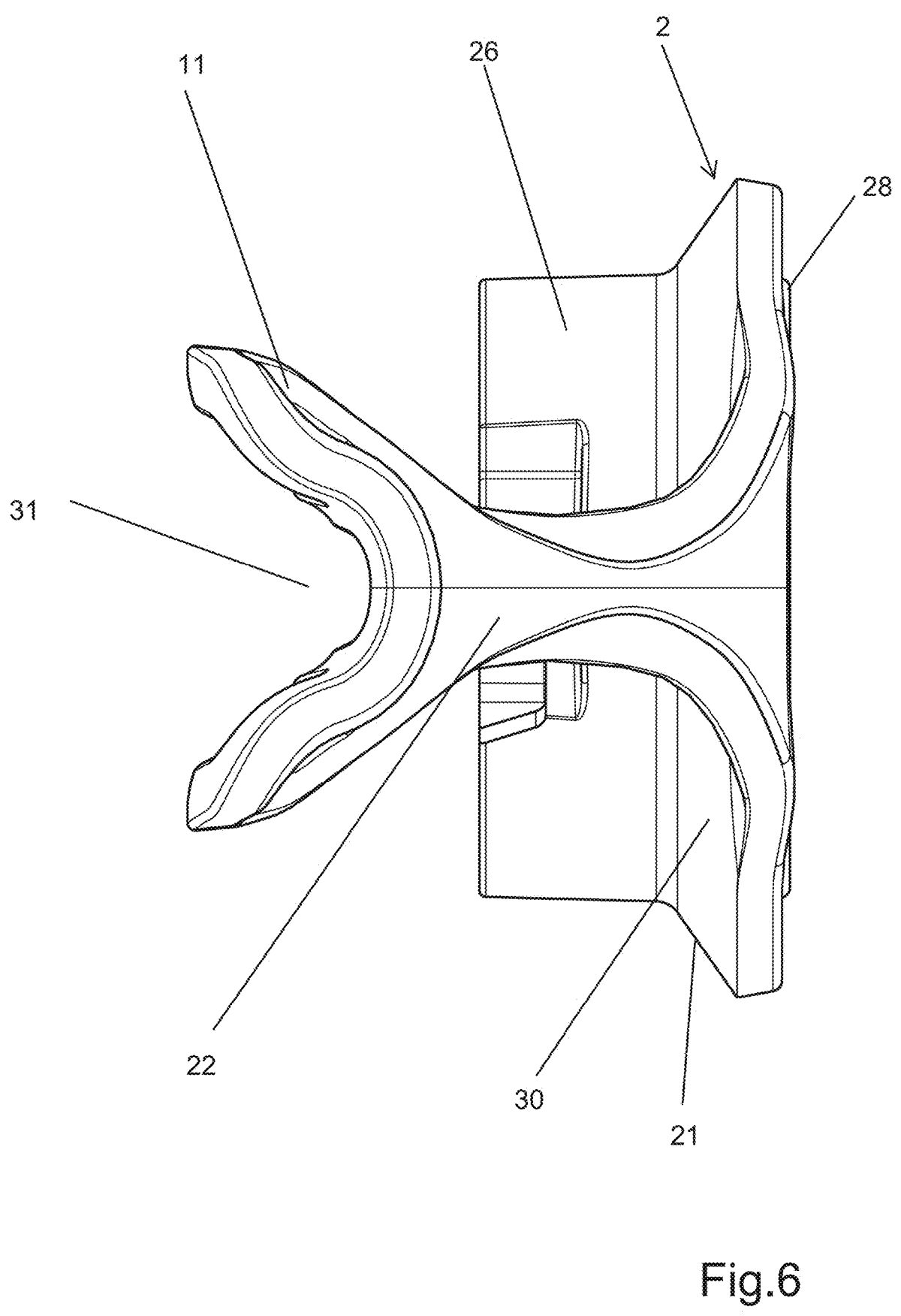

FIG. 6 shows the forehead support (2) from above. It reveals that the head part of the forehead support (2) protrudes toward a patient in relation to the forehead support connector (21). The shape of the head of the forehead support (2) accommodating the strap coupling (11) has a recess (31) which affords a space between the forehead of a patient and the strap coupling (23) in the forehead support (2).

Figure 7:
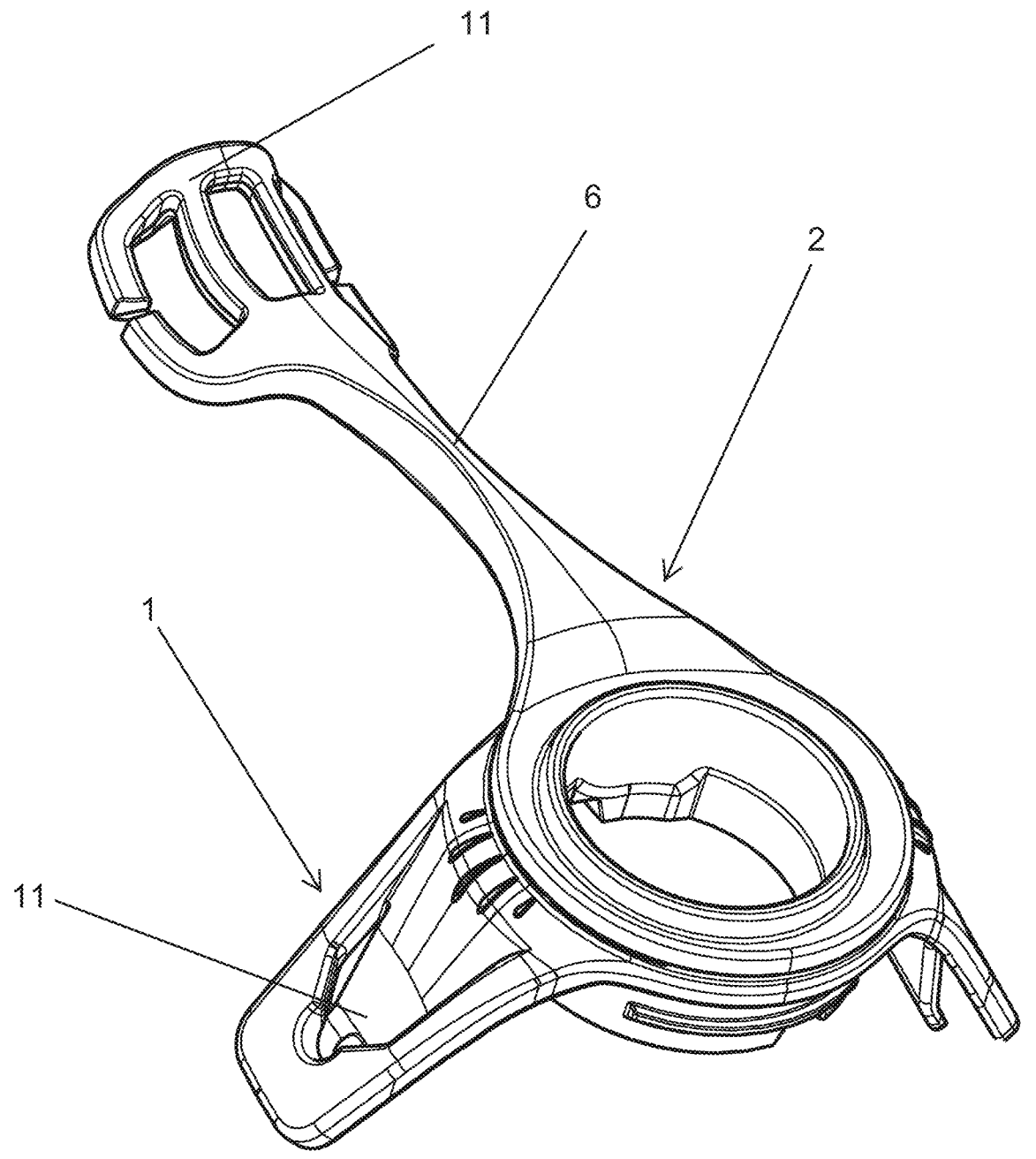
FIG. 7 shows a perspective view of mask body and forehead support as as assembled module.

FIG. 7 shows a perspective view of mask body (3) and forehead support (2) as an assembled module. In a rotationally symmetrical configuration of the mask body (3), the latter can be connected to the forehead support (2) in precisely two positions which are offset by 180° and which are functionally identical. It is thereby possible to achieve a simplification of the assembly of the modules of the respiratory mask. Mask body (3) and forehead support (2) can be connected using spacer elements (40, 41) which are arranged in the interface. Alternatively, the mechanical coupling can also be effected without using spacer elements (40, 41).

Figure 8:
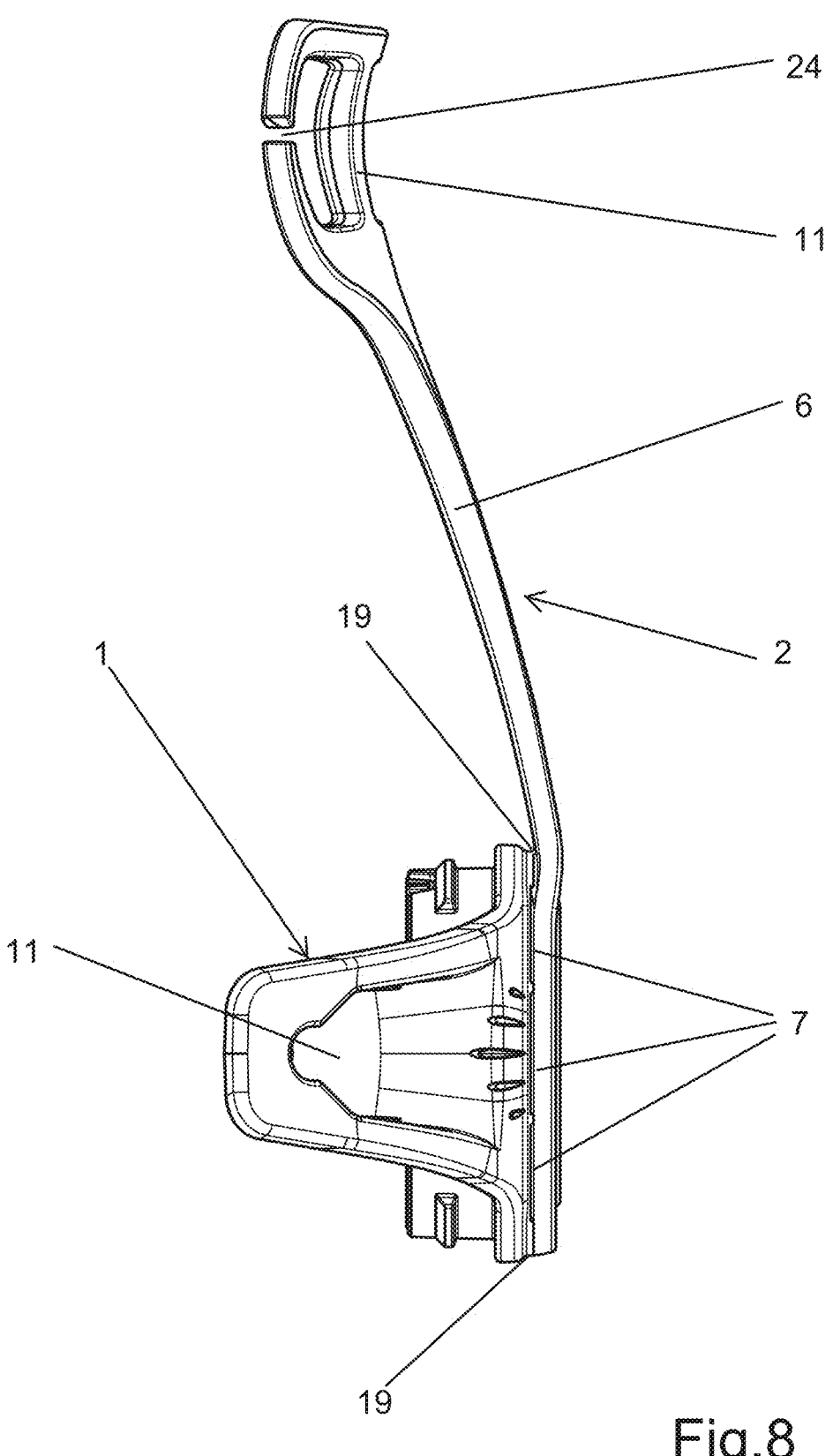
FIG. 8 shows a side view of the assembled module of mask body and forehead support.

FIG. 8 shows a side view of the assembled module of mask body (3) and forehead support (2). The gaps (17) remaining between the discharge surfaces of the mask body (3), and between the outflow channels and the discharge surface (30) of the forehead support connector (21), serve as a guide structure for the exhaled air. By means of the elevated structure in the region of the channels (19) in the mask body (3), sealing of the exhalation gap in a defined region is achieved at the upper side in the direction of the forehead support (2). This serves to avoid air being discharged into regions where it is uncomfortable for a patient, in particular the eyes.

Figure 9:
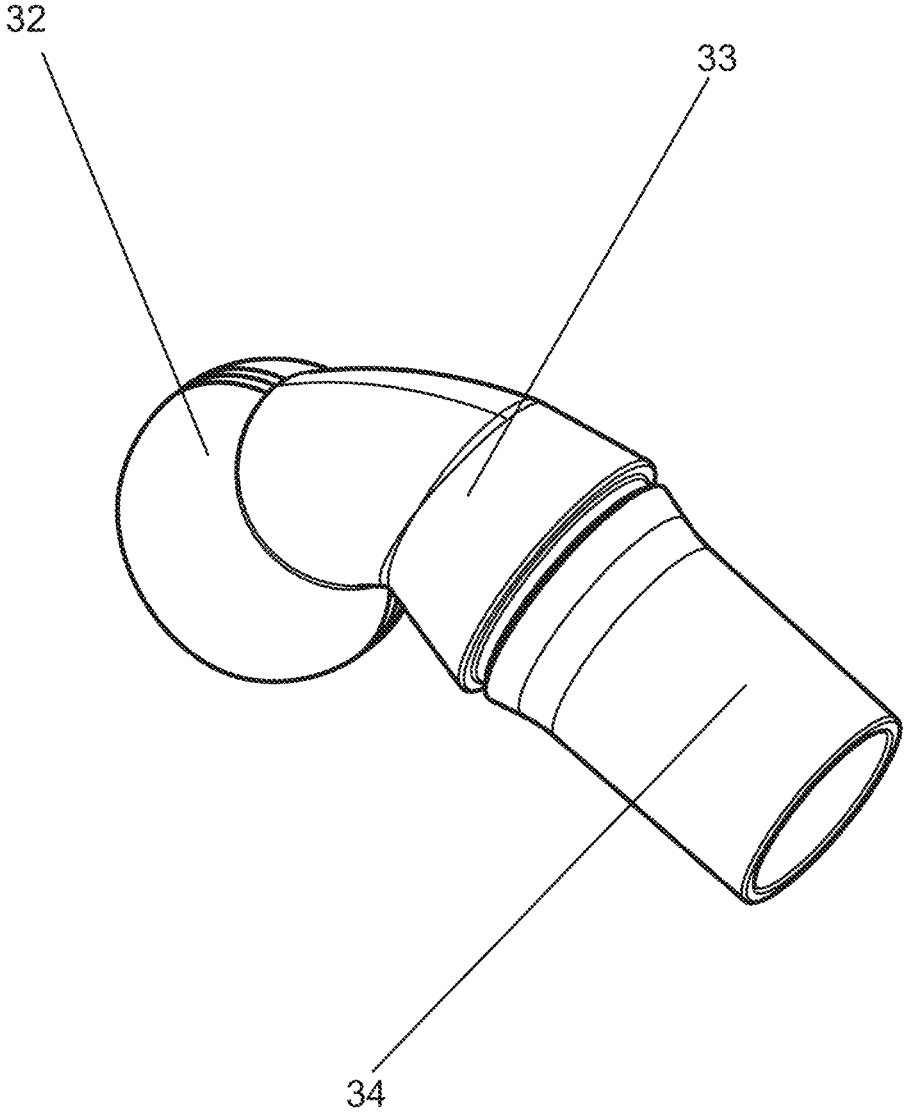
FIG. 9 shows a perspective view of an attachment piece according to the invention.

FIG. 9 shows a perspective view of an attachment piece (33) according to the invention. The attachment piece is configured as an angled tube structure and has, at one end, a surface contour (32) that corresponds to a partial sphere. This partial sphere (32) serves for the movable connection of attachment piece and forehead support (2) by means of the ball cage (27) formed in the forehead support connector (21).

At the other end, a rotatably mounted sleeve (34) is provided as attachment for a hose (not shown).

Figure 10:
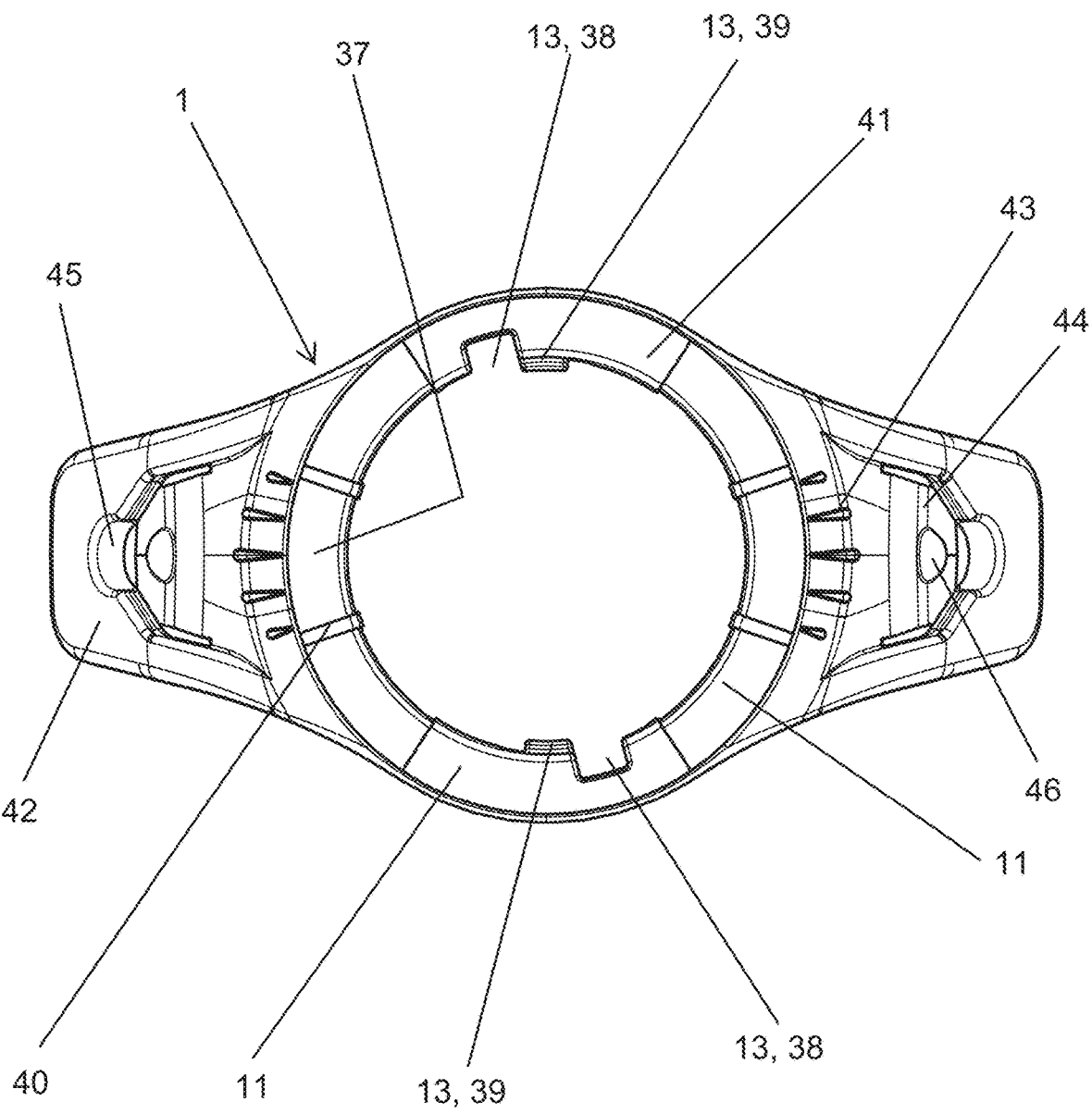
FIG. 10 shows a front view of the mask body.

FIG. 10 shows a front view of the mask body (3). It reveals the rotational symmetry through 180° about an axis located at the center point of the inner radius and protruding perpendicularly from the drawing plane. It reveals the spacer ribs (40) protruding radially from the inner contour (37), and the strengthened regions (41) about the outflow channels (8, 38). The shape of the locking tooth for the bayonet catch can also be seen, by means of which locking tooth the bayonet connection, produced by the engagement with the mating piece on the forehead support (2), is secured against unwanted rotation and release.

Several outflow surfaces (37) can be seen on the inner surface of the mask body (3). The inner surface of the mask body (3) opens up in a funnel shape toward the front, while its basic shape in the rear region directed toward a patient is defined by a tube of constant diameter. In the inner contour of the mask body (3) there are at least two channels (8, 38), which are each realized as a cutout in the tubular region and extend into the funnel-shaped region. These channels (8, 38) have a dual function both as seats for the mechanical coupling of the forehead support (2), which coupling can be configured for example as a bayonet catch, and also as discharge channels for exhaled respiratory gases, the complete contour of which discharge channels is defined jointly by mask body (3) and forehead support (2). For the bayonet catch, a tooth (39) is provided in the rear region alongside each channel (8, 38), which tooth (9) protrudes radially inward from the inner contour of the mask body (3) and affords the necessary mechanical resistance for the catch.

Furthermore, several spacer ribs (40) are arranged on the inner surface of the mask body (3) and permit a connection of mask body (3) and forehead support (2) without play and/or with pretensioning. In the region (41) of the discharge channels (8, 38), the material in the ring and funnel region is strengthened according to the height of the spacer ribs (40). Moreover, the spacer ribs (40) and the strengthened regions (41) laterally delimit the outflow surfaces (37).

Additional cutouts in the funnel-shaped region of the inner surface of the mask body (3) are also conceivable in order to form one or more additional outflow channels.

A depression extending in a ring shape within the inner contour of the mask body (3) is also conceivable, which depression distributes the outflowing exhaled gases uniformly onto the provided outflow surfaces (7). This could be realized, for example, in the transition region from the tube shape to the funnel shape of the inner surface of the mask body (3).

At its sides, the mask body (3) has two wings (7, 9, 42), which each have a mechanical structure for receiving a strap coupling (11). The strap coupling can be provided, for example, by a clip (not shown). In the front region of the mask body (3), the latter is provided with knobs (43) at the level of the wings (42), which knobs (43) permit a better grip during the handling of the respiratory mask. The knobs can also be configured as rays or arrows that indicate the direction of the outflowing respiratory gases (43).

The channel (38) and is supplemented in its basic shape behind the tooth (39) to form an L-shaped cutout, which permits the typical plug and screw connection. In the contour region behind the tooth (39), a locking tooth is provided which secures the connection.

In one embodiment of the respiratory mask, a mechanical coding can additionally be realized in the mask body (3) in such a way that the mask cushion can be connected to the mask body (3) only in intended positions. This connection is effected by plugging the mask cushion onto the outer contour (16) of the mask body (3). In the embodiment shown, the connection is secured by at least one undercut on the outer contour of the mask body (3). Besides the circular outer contour illustrated, other configurations are also conceivable. In particular, an oval shape of the outer contour is conceivable. In combination with the shape of the connection opening of the mask cushion, which connection opening can also be shaped differently with an inner circumference smaller than or equal to the outer contour of the mask body (3), the stiffness and the ratio of height and width of the mask cushion can be adjusted. In particular, a combination of an oval configuration of the outer contour and a circular configuration of the connection opening of the mask cushion is conceivable.

Besides the illustrated connection of mask cushion and mask body (3) by an undercut, other options are also conceivable. For example, bonding of the modules with the aid of a two-component adhesive is also possible.

The mechanical receiving structure provided in the region of the wings (42), and serving for the strap coupling, consists principally of a spring plate (44) in combination with a cutout in the structure of the wing (42). The clip is held in the receiving structure by a securing means (46). The securing means preferably has a radius.

What is claimed is:

1. A respiratory mask, wherein the mask comprises an interface for connecting of at least two components, wherein the interface is round or oval, the at least two components each providing at least one subregion of the interface, wherein a first one of the two components has a grip part which extends radially outward from a first one of the subregions and is configured as a pressing surface or gripping element for fingers or a hand of an operator, a second one of the two components has two grip parts which extend radially outward from a second one of the subregions and are configured as a pressing surface or gripping elements for fingers or a hand of the operator, the grip part of the first component being configured as part of a forehead support and being formed integrally with the forehead support and/or the two grip parts of the second component being configured as part of a mask body and being formed integrally with the mask body, and wherein the first and second subregions are in form-fit engagement with each other in an assembled state and are movable about a rotation axis which is perpendicular to the first and second subregions, for which purpose the grip part of the first one of the two components is rotatable to different rotation positions relative to the two grip parts of the second one of the two components.

2. The mask of claim 1, wherein the grip part of the first component and the grip parts of the second component are dimensioned such that fingers of an operator find sufficient space on them.

3. The mask of claim 1, wherein the grip part of the first component is configured as part of a forehead support and is formed integrally with the forehead support.

4. The mask of claim 3, wherein the two grip parts of the second component are configured as part of a mask body and are formed integrally with the mask body.

5. The mask of claim 1, wherein the two grip parts of the second component are configured as part of a mask body and are formed integrally with the mask body.

6. The mask of claim 1, wherein surfaces of the grip part of the first component and/or the grip parts of the second component are provided with friction-enhancing elements to improve haptics thereof.

7. The mask of claim 6, wherein the friction-enhancing elements comprise knobs.

8. The mask of claim 6, wherein the friction-enhancing elements comprise ribs.

9. The mask of claim 1, wherein the grip part of the first component is longer than a diameter of the interface.

10. The mask of claim 9, wherein the grip parts of the second component are each 50% to 200% of the diameter of the interface.

11. The mask of claim 1, wherein the grip parts of the second component are each 50% to 200% of a diameter of the interface.

12. The mask of claim 1, wherein the two grip parts of the second component are arranged symmetrically opposite each other on the second component.

13. The mask of claim 1, wherein the interface is round.

14. A respiratory mask, wherein the mask comprises an interface for connecting of at least two components, wherein the interface is round or oval, the at least two components each providing at least one subregion of the interface, wherein a first one of the two components has a grip part which extends radially outward from a first one of the subregions and is configured as a pressing surface or gripping element for fingers or a hand of an operator, a second one of the two components has two grip parts which extend radially outward from a second one of the subregions and are configured as a pressing surface or gripping elements for fingers or a hand of the operator, the grip part of the first component being longer than a diameter of the interface and/or the grip parts of the second component being each 50% to 200% of the diameter of the interface, and wherein the first and second subregions are in form-fit engagement with each other in an assembled state and are movable about a rotation axis which is perpendicular to the first and second subregions, for which purpose the grip part of the first one of the two components is rotatable to different rotation positions relative to the two grip parts of the second one of the two components.

15. The mask of claim 14, wherein the grip part of the first component is longer than the diameter of the interface.

16. The mask of claim 15, wherein the grip parts of the second component are each 50% to 200% of the diameter of the interface.

17. The mask of claim 14, wherein the grip parts of the second component are each 50% to 200% of the diameter of the interface.

18. The mask of claim 14, wherein the interface is round.

19. The mask of claim 14, wherein the interface is oval.

20. The mask of claim 14, wherein the two grip parts of the second component are arranged symmetrically opposite each other on the second component.

* * * * *